United States Patent [19]

Mifsud et al.

[11] Patent Number: 5,801,297
[45] Date of Patent: Sep. 1, 1998

[54] METHODS AND DEVICES FOR THE DETECTION OF ODOROUS SUBSTANCES AND APPLICATIONS

[75] Inventors: Jean Christophe Mifsud, Saint-Jean; Laurent Moy, Toulouse, both of France

[73] Assignee: Alpha M.O.S., Toulouse, France

[21] Appl. No.: 615,308

[22] PCT Filed: Sep. 16, 1994

[86] PCT No.: PCT/FR94/01085

§ 371 Date: Mar. 15, 1996

§ 102(e) Date: Mar. 15, 1996

[87] PCT Pub. No.: WO95/08113

PCT Pub. Date: Mar. 23, 1995

[30] Foreign Application Priority Data

Sep. 17, 1993 [FR] France ................................ 93 11291

[51] Int. Cl.⁶ .................................................. G01N 33/00
[52] U.S. Cl. ............................................ 73/23.34; 73/31.05
[58] Field of Search ................................ 73/23.34, 31.05

[56] References Cited

U.S. PATENT DOCUMENTS

| | | | |
|---|---|---|---|
| 4,457,161 | 7/1984 | Iwanaga et al. | 73/31.05 |
| 4,542,640 | 9/1985 | Clifford | 73/31.05 X |
| 4,584,867 | 4/1986 | Forster | 73/31.05 X |
| 4,586,143 | 4/1986 | Kaneyasu et al. | 73/31.05 X |
| 4,638,443 | 1/1987 | Kaneyasu et al. | 73/31.05 X |
| 4,770,027 | 9/1988 | Ehara et al. | 73/23.34 |
| 4,884,435 | 12/1989 | Ehara | 73/23.34 |
| 4,888,295 | 12/1989 | Zaromb et al. | 73/31.02 X |
| 4,895,017 | 1/1990 | Pyke et al. | 73/24.06 |
| 5,090,232 | 2/1992 | Wakabayashi et al. | 73/23.34 |
| 5,106,756 | 4/1992 | Zaromb | 73/23.41 X |
| 5,145,645 | 9/1992 | Zakin et al. | 73/31.05 X |
| 5,177,994 | 1/1993 | Moriizumi et al. | 73/23.34 |
| 5,239,483 | 8/1993 | Weir | 73/23.35 X |

FOREIGN PATENT DOCUMENTS

| | | |
|---|---|---|
| 0 239 233 | 2/1987 | European Pat. Off. . |
| 0 317 299 | 11/1988 | European Pat. Off. . |
| 0 398 687A3 | 5/1990 | European Pat. Off. . |
| 0 431 910A1 | 12/1990 | European Pat. Off. . |
| 445927 | 9/1991 | European Pat. Off. ........... 73/23.34 |
| 22550 | 1/1990 | Japan ................................ 73/23.34 |
| 38853 | 2/1990 | Japan ................................ 73/23.34 |
| 73144 | 3/1990 | Japan ................................ 73/23.34 |
| 115742 | 4/1990 | Japan ................................ 73/23.34 |
| 186139 | 7/1992 | Japan ................................ 73/23.34 |
| 10904 | 1/1993 | Japan ................................ 73/23.34 |
| 10905 | 1/1993 | Japan ................................ 73/23.34 |
| 12580 | 1/1993 | Japan ................................ 73/23.34 |
| 2 155 185 | 2/1985 | United Kingdom . |
| WO90/08314 | 7/1990 | WIPO . |

OTHER PUBLICATIONS

IEE Proceedings, vol. 137, Pt. G, No. 3, Jun., 1990: An electronic nose: a sensitive and discriminating substitute for a mammalian olfactory system.

TRAC: Trends in Analytical Chemistry, Vo. II, No. 2, Feb., 1992: Persaud, Krishna C., Electronic gas and odour detectors that mimic chemoreception in animals, pp. 61–67.

Primary Examiner—Hezron E. Williams
Assistant Examiner—Daniel S. Larkin
Attorney, Agent, or Firm—D. Peter Hochberg; Mark Kusner

[57] ABSTRACT

Device for carrying out a method of odor detection comprising, in particular, a plurality of chambers (1, 2, 2a, 3), each including a plurality of semi-conductor gas sensors (6), conductive polymer gas sensors (7), surface acoustic wave gas sensors (8), as detection means, a variable flow gas pump (10) for forming a gas flow in said chambers (1, 2, 2a, 3), measurement electronic device (16) for operating the detection means (6, 7, 8), a data processing unit (15) for recording in a file the olfactory prints obtained using the detection means, and for comparing the detected impressions with those in the file so that odors may be identified and recognized. Applications, especially to drugs, explosives, body odours and food seals.

20 Claims, 10 Drawing Sheets

METHODS AND DEVICES FOR THE DETECTION OF ODOROUS SUBSTANCES AND APPLICATIONS

BACKGROUND OF THE INVENTION

1. Field of the Invention

This invention relates to diverse fields, like the food industry, the cosmetic industry, the perfume and scent industry, the chemical industry, the packaging industry and the environment, and, more generally, to all fields in which the detection of odors and odorous substances or volatile substances, referred to generally, and without distinction, in the rest of this specification as odorous substances or odors, contributes means of investigation, of monitoring and action in these fields.

2. Description of the Prior Art

The detection of odorous substances has many industrial applications, especially in processes in the foodstuff industry, in which one can, for example, determine the degree of freshness and the quality of the products, thanks to the odorous substances which they release. Gas chromatography, which consists in a method of selective detection by separating the molecules of gas compositions, is used as a way of monitoring odors. However, this method has many drawbacks; in effect, the detection results of the substances vary according to the method of sampling chosen, the time taken to achieve the results is relatively long, and the cost of gas chromatography equipment added to the cost of a mass spectrometer necessary to analyze the results is high.

Recent developments in the field of detection of odorous substances propose, as means of detecting odorous substances, detection methods and apparatus using semiconductive gas-sensors. The odorous substances change the electrical properties of the semiconductors by making their electrical resistances vary, and the measurement of these variations allows one to determine the concentration of odorous substances. These methods and apparatus used for detecting odorous substances use a relatively brief detection time, of around a few seconds, compared to those given by gas chromatography, which takes from several minutes to several hours. On the other hand, the semiconductive gas-sensors must operate at a high temperature, around 350° C. Moreover, the sensors have good sensitivity but a mediocre selectivity with regard to odorous substances.

Other recent gas sensor technologies are now used, leading to other methods and apparatus for detecting odorous substances. One finds, for example, apparatus having conductive-polymer gas-sensors and apparatus having surface-acoustic-wave gas-sensors.

The conductive-polymer gas-sensors have a film made of a conductive polymer sensitive to the molecules of odorous substances. On contact with the molecules, the electric resistances of the sensors change and the measurement of the variation of this resistance enables the concentration of the odorous substances to be determined. An advantage of this type of sensor is that it functions at temperatures close to room temperature. One can also obtain, according to the chosen conductive polymer, different sensitivities for detecting different odorous substances. In general, conductive-polymer sensors have better selectivity but are less sensitive than the semiconductive sensors.

The surface-acoustic-wave gas-sensors generally include a substrate with piezo-electrical characteristics covered by a polymer coating which is able to absorb the odorous substances. The variation of the resulting mass leads to a variation of its resonant frequency. This type of sensor allows for very good mass-volume measures of the odorous substances.

The methods and apparatus for detecting odorous substances that one normally encounters generally include several sensors so as to augment the selectivity of the odorous substances, but all of the sensors use the same technology, that is to say either semiconductive or conductive-polymer or surface-acoustic-wave technology. Because of this, the possibility of detecting odorous substances is limited to the level of sensitivity and the discrimination given by the sensors of one technology. Moreover, these apparatus use methods of transporting the odorous substances by natural convection, in a detection enclosure comprising the sensors, which increases to an appreciable extent the time it takes to sense the odorous substances and, thus, the duration of the detection processes, and this to a greater degree when the volatility of the product being tested is weak.

SUMMARY OF THE INVENTION

The present invention allows these disadvantages to be overcome, more precisely, it consists of a process for detecting odorous or volatile substances characterized by the fact that it comprises the following steps:

providing at least a first and a second enclosure with respective first and second detection means; the first detection means comprising a plurality of semiconductive gas-sensors, or a plurality of conductive-polymer gas-sensors or a plurality of surface-acoustic-wave gas-sensors; the second detection means comprising a plurality of semiconductive gas-sensors, or a plurality of conductive-polymer gas-sensors, or a plurality of surface-acoustic-wave gas-sensors; these semiconductive gas-sensors, conductive-polymer gas-sensors and surface-acoustic-wave gas-sensors having electrical or piezo-electrical properties which are sensitive to the molecules of the odorous or volatile substances, testing the electrical or piezo-electrical properties of each of the first and second detection means, these latter being in contact with a variable controlled flow of gas, in order to initialize the first and second detection means before said odorous or volatile substances are present, transporting said odorous or volatile substances of a first sample into at least said first and second enclosures, in the variable controlled flow of gas, measuring, during a determined interval of time, the electrical or piezo-electrical properties of each of said first and second detection means, in the presence of the variable controlled flow of gas, comprising said odorous or volatile substances, relative to said initialization of the first and second means of detection, in order to obtain qualitative and quantitative data on said odorous or volatile substances, cleaning these first and second detection means by sweeping them with a gas, in order to initialize the first and second detection means.

The transport of the odorous substances from a sample in a variable controlled flow of gas allows for very rapid detection of odorous substances, in about a few seconds. Moreover, this feature allows the transport conditions of odorous substances in a biological nose to be approached and enables the reproducibility of the methods of detection according to the invention to be assured by controlling the conditions of transport of the odorous substances, which is not the case in the methods of the past where the means of natural convection is not controlled.

The means used in order to achieve this variable controlled flow of gas are advantageously made up of at least a pump with variable flow rate; this pump being advantageously used in order to establish a variable controlled flow of gas during the testing of the electrical and/or piezoelectrical properties and the cleaning of the detection means. The gas used can be the surrounding air or purified air. During the phase of measuring the electrical and/or piezoelectrical properties, the gas flow rate can be diminished or increased according to whether the odorous substances become more or less volatile throughout the duration of the measurement period.

According to an advantageous characteristic, this invention provides for a third enclosure with third detection means; this third detection means comprising a plurality of semiconductive gas-sensors or a plurality of conductive-polymer gas-sensors or a plurality of surface-acoustic-wave gas-sensors.

The point of this characteristic is to provide the method according to the invention with three different means of detection in order to obtain better sensitivity and better general selectivity of detection. In fact, as has been explained at the beginning of the description, the different types of sensors, with semiconductive, conductive polymer or surface acoustic wave technology, each have different characteristics which are complementary: good sensitivity (semiconductive sensors), good selectivity (conductive-polymer sensors), and good mass/volume measurement (surface-acoustic-wave sensors).

According to an advantageous feature, the process according to the invention includes at least a recording of said qualitative data of these odorous substances at a determined instant in time in order to make up a file or catalogue of the odorous substances.

This feature allows a file or catalog to be established, notably using a data processing system, in which the data furnished by the measurements performed on known odorous substances is recorded in the form of olfactory characteristics. Thus each of the odorous substances is characterized by its own olfactory characteristic; this olfactory characteristic being comprised of the data provided by each of the detection means. This olfactory characteristic can evolve throughout the duration of the measurement period, notably according to the degree of volatility of the odorous substances or the value of the variable gas flow rate.

An operator can advantageously visualize the measurement information by using a monitor connected to the data processing system; this data can be presented in any of the known and wide-spread forms such as histograms, curves, clusters of points, star diagrams, and all sorts of two-dimensional and three-dimensional representations.

According to an advantageous feature, the process of the invention includes at least the following supplementary stages:

transporting said odorous or volatile substances from a second sample into the first and second enclosures, within a controlled variable flow of gas, measuring the electrical or piezo-electrical properties, during a determined time interval, of each of the first and second detection means in the presence of the controlled variable flow of gas containing said odorous and volatile substances, relative to said initialization, in order to obtain qualitative and quantitative data on said odorous or volatile substances, comparing said data with the file of odorous and volatile substances, simultaneously or after the measurements themselves, this comparison occurring, at most, during the total duration of the measurement period, so as to at least identify, and at the most recognize, by means of a neural network, the odorous or volatile substances detected.

The creation of a file of olfactory characteristics provides the possibility of introducing a comparison step into the process according to this invention, in order to detect odorous substances of products unknown to the operator. The measurement data constituting an olfactory characteristic at a particular instant, can be advantageously transmitted, throughout the duration of the measurement interval of the unknown product to the data processing system, which compares the characteristic to those already in the file, which informs the operator, for example by use of a monitor, that what is present are either odorous substances which are known and, hence, present in the file or are unknown odorous substances which are, thus, absent from the file. In the case of odorous substances which are recognized by the data processing unit, the identity of these substances can be communicated to the operator. In the alternative case, the data processing system informs the operator of odorous substances which are unknown in the file. This step of comparison and recognition of odorous substances is achieved by a software program, advantageously neural network software.

The operator can choose to register the unknown substance or substances and create a new olfactory characteristic in the file, for example, with the goal of identifying the same substances at a later time. In effect, the comparison step can consist of a simple identification of unknown odorous substances, based on an olfactory characteristic present in the file, this comparison step not requiring use of neural network software.

This simple comparison of the olfactory characteristics provides the practical advantages of being able to identify two or more products as being similar because they possess identical olfactory characteristics.

It should be noted that in the case where the comparison of measurement data with the file of odorous substances occurs after the measurements themselves are taken, it is necessary to record these measurements.

According to other features, the process of detecting odorous substances following this invention includes means of separating the odorous substances, these separation means advantageously including a gas chromatography device.

These features enable a molecular olfactory characteristic to be obtained of the odorous substances. These means of separating by gas chromatography occur before said means of detection.

In this case, the conventional gas chromatography device first separates the different molecules of the odorous substances which are then transported by molecule type toward the detection means, these detection means then allow an olfactory characteristic to be obtained for each of the molecular types, following one of the processes of this invention described above. This process according to the invention notably enables the advantages of gas chromatography (molecular separation) to be associated with the present detection means, so as to constitute a file of olfactory molecular characteristics.

The invention also has as an object an apparatus for detecting odorous or volatile substances enabling the above-described methods of detecting odorous and volatile substances to be put into practice, as well as the applications noted at the end of the description.

Other advantages and characteristics will become apparent from the description to follow, of two examples of embodiments of apparatus for detecting odorous or volatile substances according to the invention, and of a few examples of applications which follow, accompanied by the appended diagrams, these examples being given for illustrative purposes without it being possible to draw any restrictive interpretation of the invention therefrom.

DETAILED DESCRIPTION OF THE PREFERRED EMBODIMENTS

Figure 1:
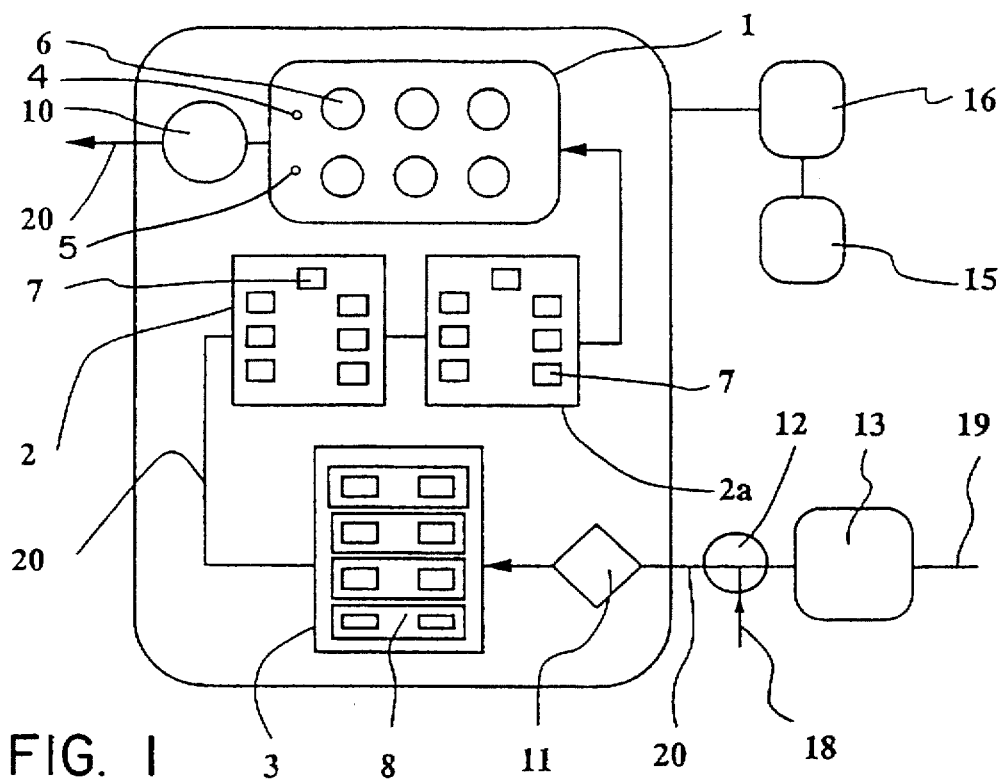
FIG. 1 shows a functional diagram of an apparatus for detecting odorous or volatile substances according to the invention, which includes four enclosures mounted in series.

The apparatus for detecting odorous substances shown in FIG. 1 includes a first, second, third, and fourth enclosures 1, 2, 3, 2a provided, respectively, with six semiconductive gas-sensors 6, six conductive-polymer gas-sensors 7, four surface-acoustic-wave gas-sensors 8, seven conductive-polymer gas-sensors 7, a pump with variable flow rate 10 for gaseous fluids, measurement electronics 15, and a data processing system 16.

The number of sensors 6, 7, 8, 7, respectively, of each enclosure 1, 2, 3, 2a is determined in a way to provide the maximum apparatus sensitivity and selectivity with regard to the odorous substances to be detected.

The four enclosures 1, 2, 3, 2a are laid out in series on a conduit/pipe 20 within which circulates a flow of gas generated by the pump 10 having a variable flow-rate, which is placed at the exit of the last enclosure with respect to the direction of circulation of the gas flow as indicated in FIG. 1. This position of the pump 10 is chosen because it does not contaminate the sensors located in the different enclosures. In this way, the pump 10 with variable flow-rate establishes a flow of gas in the four enclosures by suction or vacuum. The different sensors 6, 7, 8 are placed in the enclosures so that they will evidently be in contact with the flow of gas. The regulatable flow of gas will advantageously be variable between 5 ml/mn and 500 ml/mn in the case where the enclosures are placed in series.

The order of placing the four enclosures 1, 2, 3, 2a on the conduit 20 is advantageously determined as a function of the disturbances induced by the sensors of each enclosure, on the gas transporting the odorous substances to be detected or on the odorous substances themselves, and as a function of their sensitivity. Consequently, in the direction of circulation of the gas flow there are encountered, as shown in FIG. 1, the third enclosure 3 equipped with surface-acoustic-wave gas-sensors 8, the second and fourth enclosures 2, 2a equipped with conductive-polymer sensors 7, and the first enclosure 1 equipped with semiconductive sensors 6; these last sensors operating at high temperatures and thus modifying the flow of gas more significantly.

On the conduit 20 at the entrance to the third enclosure 3, a filter 11 insures a certain purity of the gas circulating in the conduit 20 and the enclosures 1, 2, 3, 2a. The filter 11 preserves the sensors 6, 7, 8 from contamination caused by impurities present in the suctioned air, for example in the surrounding air in an appropriate case, but evidently allows the passage of the odorous substances.

Upstream of the filter 11 in the direction of circulation of the gas flow, and connected onto the conduit 20, there is a three-way valve 12 that allows a selection either of suction of the gas through the conduit 18 connected to the surrounding air or of suction from a chamber 13 for samples comprising the odorous substances or the products whose odorous substances it is desired to detect. This chamber 13 is connected by the conduit 19 to the air in the environment.

The suction through the conduit 18 is notably used for the testing stage of electrical and/or piezo-electrical properties of the sensors 6, 7, 8 and the stage of cleaning the gas sensors 6, 7, 8 after a passage of the odorous substances through the enclosures 1, 2, 3, 2a.

The suction through the conduit 19 is notably used for the step of measuring the electrical and/or piezo-electrical properties of the gas sensors 6, 7, 8 in the presence of the variable controlled flow of gas containing the odorous substances. In this way, in its passage through the sample chamber 13, the air carries away the odorous substances, then goes through the filter 11 and the four enclosures 3, 2, 2a, 1, housing the gas sensors 8, 7, 6 respectively, before going through the pump 10 and being rejected to the exterior of the detection apparatus. It can prove necessary to heat the product placed in the chamber 13 in order to generate or accelerate the production of the odorous substances, especially if the product is of low volatility. In this case, the chamber 13 can include any kind of non-polluting heating system, such as for example electrical heating by resistance.

It should be mentioned that the presence of chamber 13 and the three-way valve 12 is dispensable to the functioning of the apparatus for detecting odorous substances according to the invention. In the absence of chamber 13 and valve 12, the suction of the gas flow or of the gas including the odorous substances occurs directly through the conduit 20 in the entrance of the apparatus or directly through filter 11. This configuration (not shown) of the apparatus according to the invention allows the apparatus to detect odorous substances present in an ambiant gas. Alternatively, a gas chromatography device could be used in place of the chamber 13 shown in FIGS. 1 and 2.

At least one temperature sensor and humidity sensor (both not shown), in order to measure respectively the temperature of the flow of gas and the level of humidity of the gas flow, are placed in at least one of the enclosures. The temperature and humidity level parameters influence the measurements of the piezo-electrical and/or electrical properties of the gas sensors 6, 7, 8, and because of this, it is necessary to know the values of these parameters in order to be able to perform comparisons of the odorous substances.

The set of gas sensors 6, 7, 8, temperature sensor 4, and humidity sensor 5 are connected to measurement electronics 15 enabling, in the processes according to the invention, the step of testing of the electrical and/or piezo-electrical properties of the gas sensors 6, 7, 8, the measuring of the temperature and the rate of humidity of the flow of gas and also the step of measuring the electrical and/or piezo-electrical properties of the gas sensors 6, 7, 8 in the presence of the odorous substances.

The electronic measuring device 15 allows for the independent application of, on the one hand, regulatable electronic voltage at the terminals of each of the sensors 6, 7, and on the other hand, a surface acoustic wave to each of the sensors 8, at least for the stage of measuring the piezo-electrical and/or electrical properties of these sensors during the execution of the processes according to the invention.

The choice of an electrical voltage applied to the sensors 6, 7 and the choice of a frequency applied to the sensors 8 in the testing stage in the absence of odorous substances but in the presence of the flow of gas determines the initialization values of these sensors, with respect to which measurements will be taken during the stage of measuring the electrical and/or piezo-electrical properties in the presence of the gas flow containing the odorous substances.

Each of the semiconductive gas sensors 6, each of the conductive-polymer gas-sensors 7, and each of the surface-acoustic-wave gas-sensors 8 give qualitative and quantitative information on the odorous substances present in the enclosures 1, 2, 3, 2a.

For the semiconductive gas-sensors 6 and the conductive-polymer gas-sensors 7, the measurement electronics 15 measures the values of the variations of resistance or voltage, or the conducting properties of these sensors, as quantitative data on the odorous substances. For the surface-acoustic-wave sensors 8, the measurement electronics 15 measures the variation of resonant frequency of the sensors 8 induced by the mass of molecules of odorous substances adsorbed by the polymer coating of the sensor, as quantitative data of the odorous substances present.

The qualitative data is furnished by the choice of the sensitive parts equipping the sensors, notably the choice of polymer for the conductive-polymer sensors 7 and the surface-acoustic-wave sensors 8, a choice made based on the needs of the user of the apparatus. For the semiconductive sensors 6, the qualitative data is furnished by the choice beforehand of the type of metallic oxide as well as, notably, the choice of their respective operating temperatures, according to the needs of the user. The temperature can be regulated independently for each semiconductive sensor 6 by way of the measurement electronics 15, during the stage of testing the electrical properties, in order to determine an optimal range of usage of the sensors; these last sensors 6 react to the different odorous substances according to whether their own temperature is more or less elevated.

It should be noted that, at all moments of the processes for detecting odorous substances according to the invention, the gas flow can be modified in a controlled way thanks to the variable flow-rate pump 10. This feature makes it possible, notably, to accelerate the detection processes in the case of detecting odorous substances of products with low volatility or to accelerate the response time of the sensors in the case of detecting odorous substances in small quantities.

The data processing unit 16 receives the qualitative and quantitative data on the different detected and measured odorous substances, which are transmitted to it by the measurement electronics 15. The data processing system 16 comprises a central unit provided with software application programs (not shown) and, advantageously, a monitor (not shown) which interfaces between said central unit and the operator. The central unit enables the step of recording the data on the measurements performed by the measurement electronics 15. This recording advantageously allows for the creation of a file of odorous substances and enables the step of comparing the measurement data with the file of odorous substances.

The measurement electronics 15 notably takes measurements on sensors 6, 7, 8, advantageously in a continuous fashion, during an interval of time determined by the operator according to his/her requirements. During this interval of time, the data processing system 16 records the information constituted by the results of the measurements in such a manner as to furnish the operator with information on the odorous substances present as a function of time. This characteristic provides some advantages which will be explained later in the examples of detecting odorous substances according to the processes of this invention, notably in the examples of detecting odorous substances of perfumes, illustrated by FIGS. 8 and 9.

The recording of the data allows the operator to be informed at every moment during the measurement time interval of the values of the instantaneous measurements from all of the sensors, the set of these instantaneous values defining an olfactory characteristic of the odorous substances at that instant. This olfactory characteristic impression can take any of the conventional forms, advantageously on a monitor (histogram, curved diagram, star diagram, etc.). The evolution of the olfactory characteristic during the course of the measurement time interval can also be shown on the monitor in many conventional ways (multiple curves, three-dimensional diagrams, etc.).

The period of comparing the measurement data with the file of odorous substances can take place in the course of the measurement time interval or can take place after the measurements. In this case, it is necessary to proceed to the recording of the measurement data during the measurement time interval.

The step of comparing the data must be differentiated according to what one wants, whether it is to identify two or more odorous substances or to recognize odorous substances.

With respect to the identification of two or more odorous substances, it suffices to have placed in the file, during at least a first detection, one or more olfactory characteristics against which it is desired to compare other odorous substances. It should be noted that the operator does not in this case necessarily need to know the identity of the odorous substances placed in the file in the form of olfactory characteristics. Later, during the subsequent detections, and with the goal of finding the recorded odorous substance or substances, the operator will compare the new characteristics, obtained as indicated in the preceding paragraphs, with the recorded ones and will make the identification, should it happen that they are the same.

It should be mentioned that the identical odorous substances may have been measured or recorded according to different quantitative data or concentrations, which makes a comparison of the olfactory characteristics more difficult, these being different despite the identity of the odorous substances. In order to obtain characteristics which are independent of the concentration, the data processing unit 16 can bring about a normalization of the data. That is to say, it can bring together all of the data of the sensors defining an olfactory characteristic, in equal proportions, until there is a unit value that can be set, advantageously, based on the sensor furnishing the largest-value data.

The recognition of odorous substances by the apparatus according to the invention is possible with the aid of supplementary means as compared with simple identification. The recognition of odorous substances requires that the apparatus has, on the one hand, a memory of all of the odorous substances to be recognized and, on the other hand, a means of discrimination, that is, a means of identifying or differentiating odorous substances having olfactory characteristics which are similar or different.

During an initial stage, it is thus necessary to place the olfactory characteristics of the odorous substances into a memory of the data processing system 16 in order to create a file of known odorous substances. The operator then associates one or more olfactory characteristics with the name of the corresponding odorous substance, in the memory of the central unit. The means of discrimination are furnished by neural network software which handles the measurement data of each of the sensors defining the olfactory characteristic in order to compare them with the data of the olfactory characteristics in the file and to identify, or differentiate, or estimate the absence of, detected odorous substances with regard to the odorous substances present in the file. The operator is informed of the results of the comparison, advantageously by means of the monitor which can, for example, display either the name of the odorous substance detected or a message "odorous substance unknown."

Once the operator has obtained the results desired, it is necessary to clean the sensors before another use. This operation occurs by means of the pump 10 with variable flow rate, such as the one indicated above, by sweeping the sensors 6, 7, 8 with a flow rate of gas which is advantageously greater, until they assume their respective initialization values given during the step when the electrical and/or piezo-electrical properties were tested. The measurement electronics 15 enables this operation to be controlled.

Figure 2:
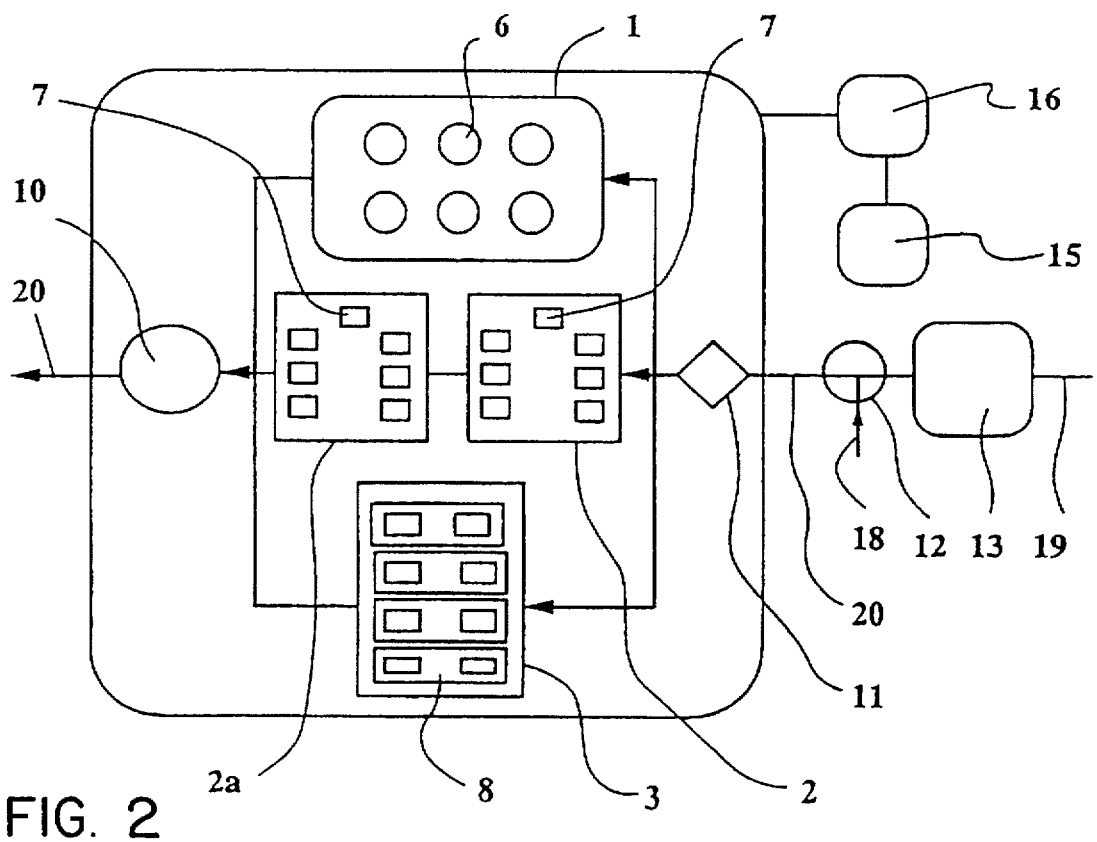
FIG. 2 shows a functional diagram of an apparatus for detecting odorous or volatile substances according to the invention, which includes four enclosures mounted in parallel to each other and in series.

FIG. 2 shows a variant of the apparatus for detecting odorous substances according to the invention illustrated in FIG. 1. It is differentiated by another arrangement of the four enclosures 1, 2, 3, and 2a. The enclosures 1, 3 and the group of the two enclosures 2, 2a are placed in parallel on the conduit 20, as shown in FIG. 2. It is to be noted that the two enclosures 2, 2a, both containing conductive polymer sensors 7, are placed in series on one of the branches of the parallel assembly. The interest of this feature is that it provides independence of the passage of the flow of gas through one enclosure compared to another which is provided with sensors of a different type of technology. In this way, one avoids the possible modifications of the gas flow from one enclosure compared with the following one in a placement in series, changes caused by the passage of the gas flow over the sensors. Moreover, there exists in this case the possibility of isolating, according to any known methods, at least one of the parallel branches of the conduit 20, then isolating at least one enclosure, if desired, by means of valves (not shown).

The pump 10, with variable flow rate used on the apparatus according to the invention shown in FIG. 2, makes it possible, in the case of enclosures placed in parallel on the conduit 20, to be able to have available advantageously a regulatable gas flow rate between 5 ml/mn (millimeters per minute) and 500 ml/mn for each enclosure.

The apparatus according to the invention can be compact and portable so that it is easier to manage. The enclosures 1, 2, 3, 2a may each have a volume on the order of a cubic centimeter, which suffices for detecting odorous substances. The data processing unit can also have very small dimensions, such as those of an electronic card. The monitor can be a liquid crystal display screen, or a diodes display screen, or a cathodic screen, of small size. Therefore, the apparatus can easily be transported to many locations by one person. In the case of detecting odorous substances present in the air, the chamber 13, the three-way valve 12, and the conduits 18, 19 are dispensable as has already been indicated earlier.

Many experiments for detecting odorous substances have been performed using the methods and apparatus according to this invention, of which certain examples, among the more representative, will be described with the aid of FIGS. 3–17.

A first experiment relates the detection and the comparison of coffee aromas and is illustrated by FIGS. 3–6.

Figure 3:
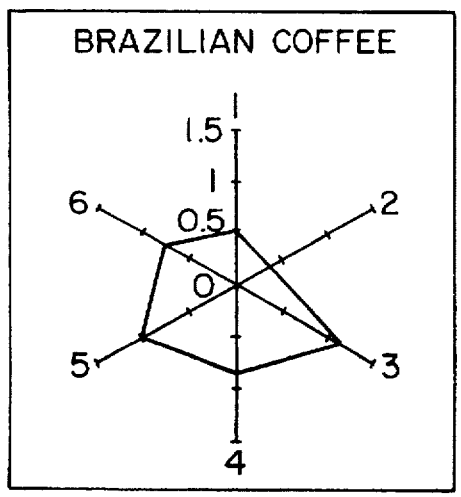
FIGS. 3-6 show four diagrams of olfactory characteristics of two different types of coffee odors.
Figure 4:
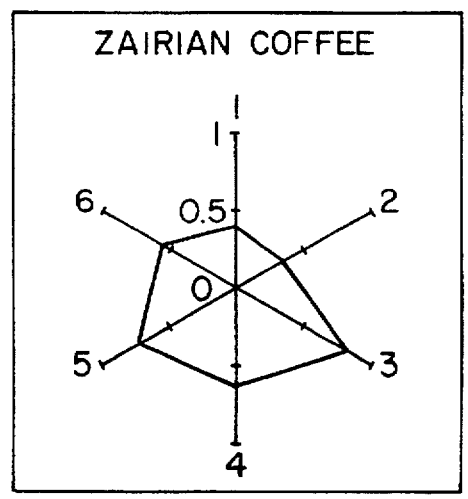

The FIGS. 3 and 4 show the olfactory characteristics of a Brazilian coffee and a coffee from Zaire, each provided by a group of six semiconductive sensors. The characteristics are shown in a star diagram, each branch corresponding to a sensor. The discrimination of the two coffees by their respective characteristics is not straightforward, taking into account the middling selectivity of this type of sensor.

Figure 5:
Figure 6:
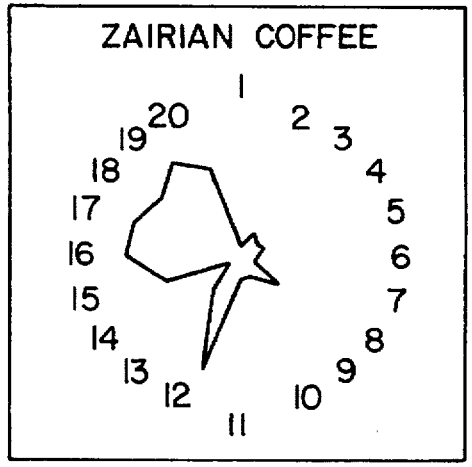

FIGS. 5 and 6 respectively show olfactory characteristics of these same coffees from Brazil and Zaire, each given by a group of six semiconductive sensors and fourteen conductive-polymer sensors. The characteristics are also shown in the form of a star, to facilitate a comparison with FIGS. 3 and 4. The references from 1–6 correspond to the semiconductive sensors, and the references 7–20 correspond to the conductive polymer sensors.

It is seen that the characteristics obtained with such a group of sensors provide easy discrimination of the two coffees, the determining element of the characteristic for the differentiation of the coffees being essentially formed by the polymer conductive sensors.

Figure 7:
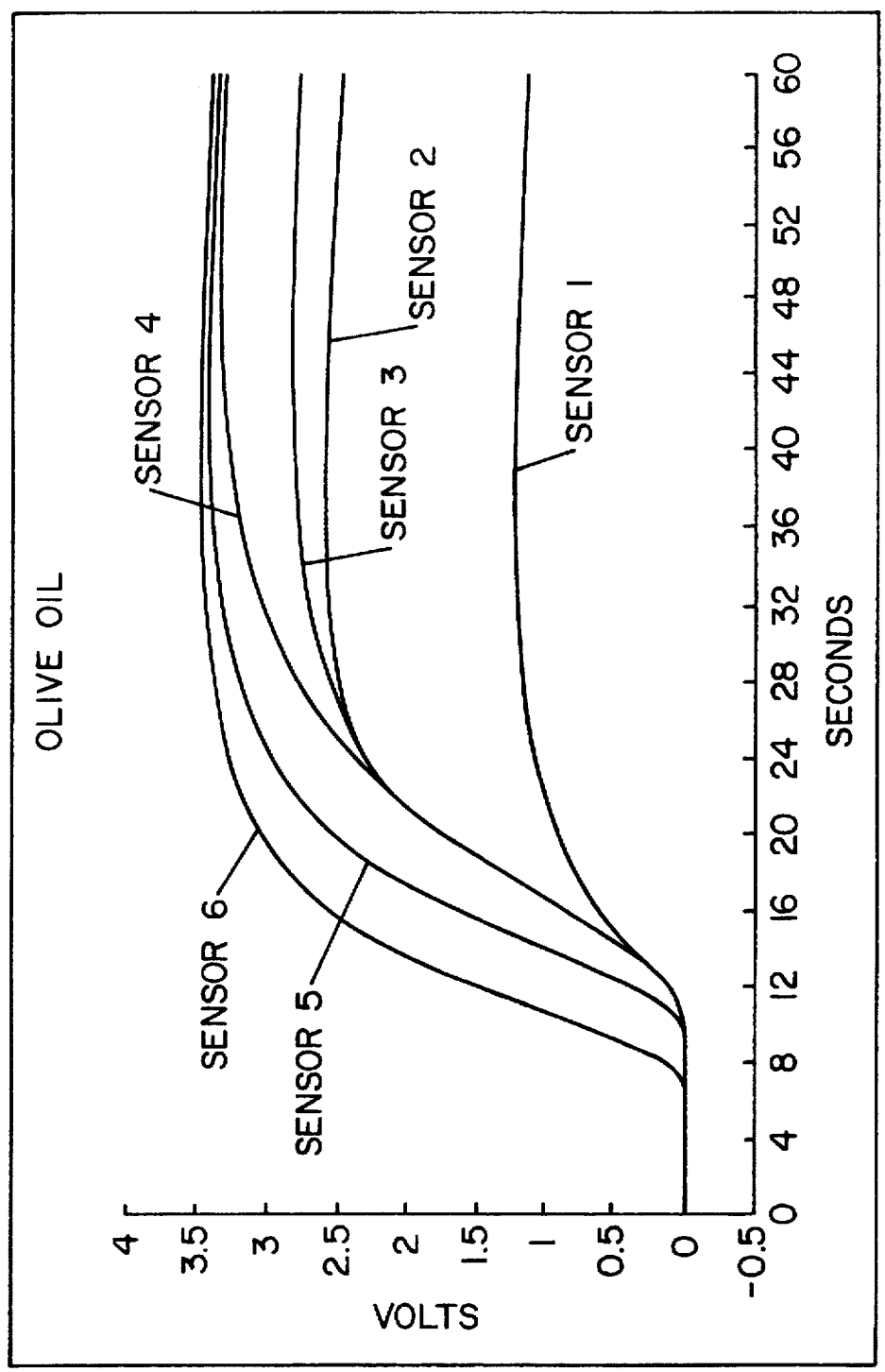
FIG. 7 shows a diagram of an olfactory characteristic over time, coming from an olive oil.

A second described experiment was performed with an olive oil, and is illustrated in FIG. 7.

FIG. 7 shows an olfactory characteristic of odorous substances from a Tuscany olive oil, this characteristic being obtained with: an enclosure equipped with six semiconductive sensors, a flow rate of air of 100 ml/mn, and an interval of time of measurement of 60 seconds. The x-axis is graduated in seconds and the y-axis is graduated in volts (voltage at the terminals of the sensors). The characteristic is made up of six curves, each one corresponding to a sensor. The diagram shows the values substantially stabilized after around 30 seconds, values which can be recorded in a file. Thirty-five different olfactory characteristics of oil (not shown) could then be differentiated.

Figure 8:
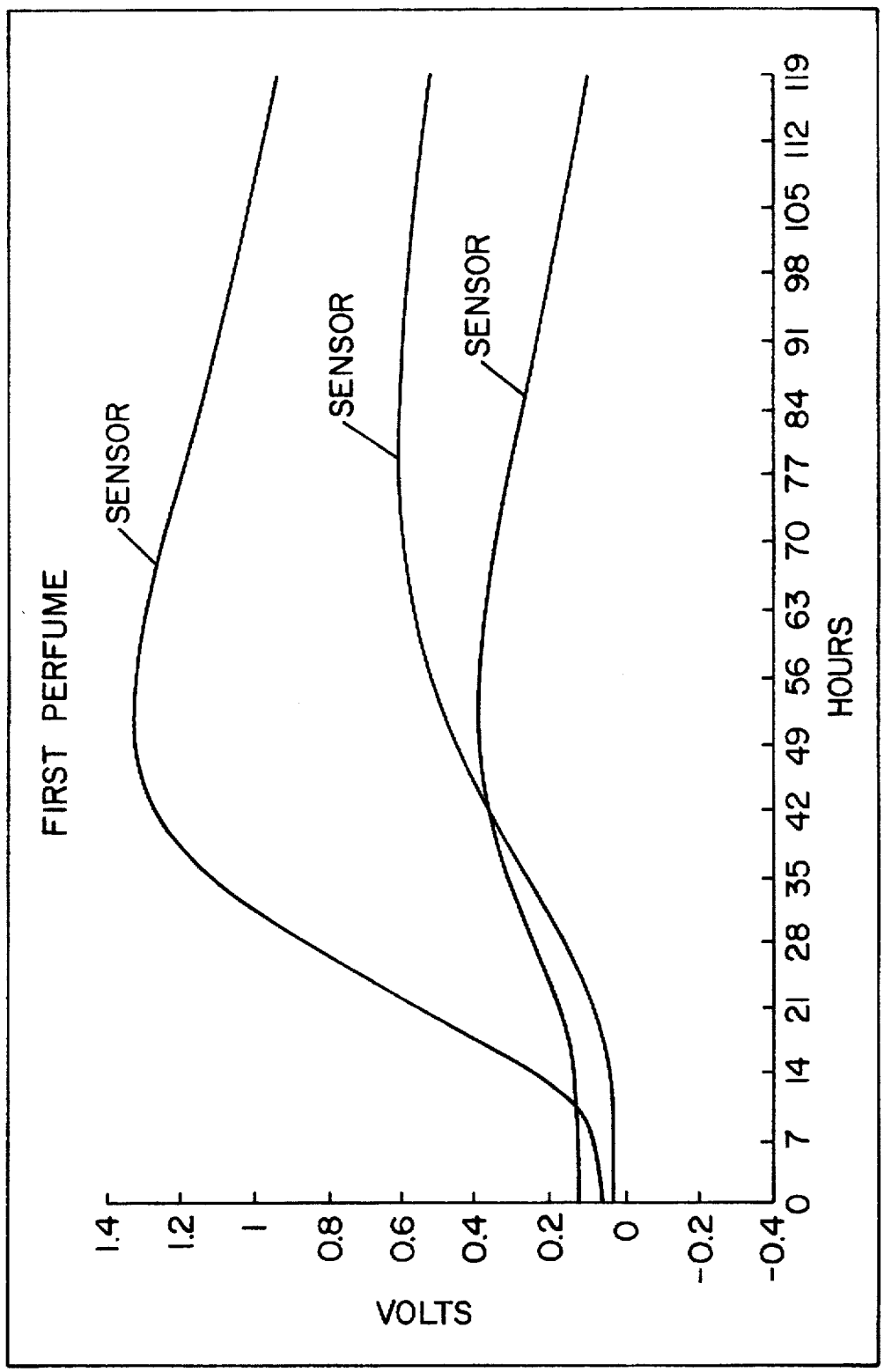
FIG. 8 shows a diagram of an olfactory characteristic of odorous substances coming from a perfume.
Figure 9:
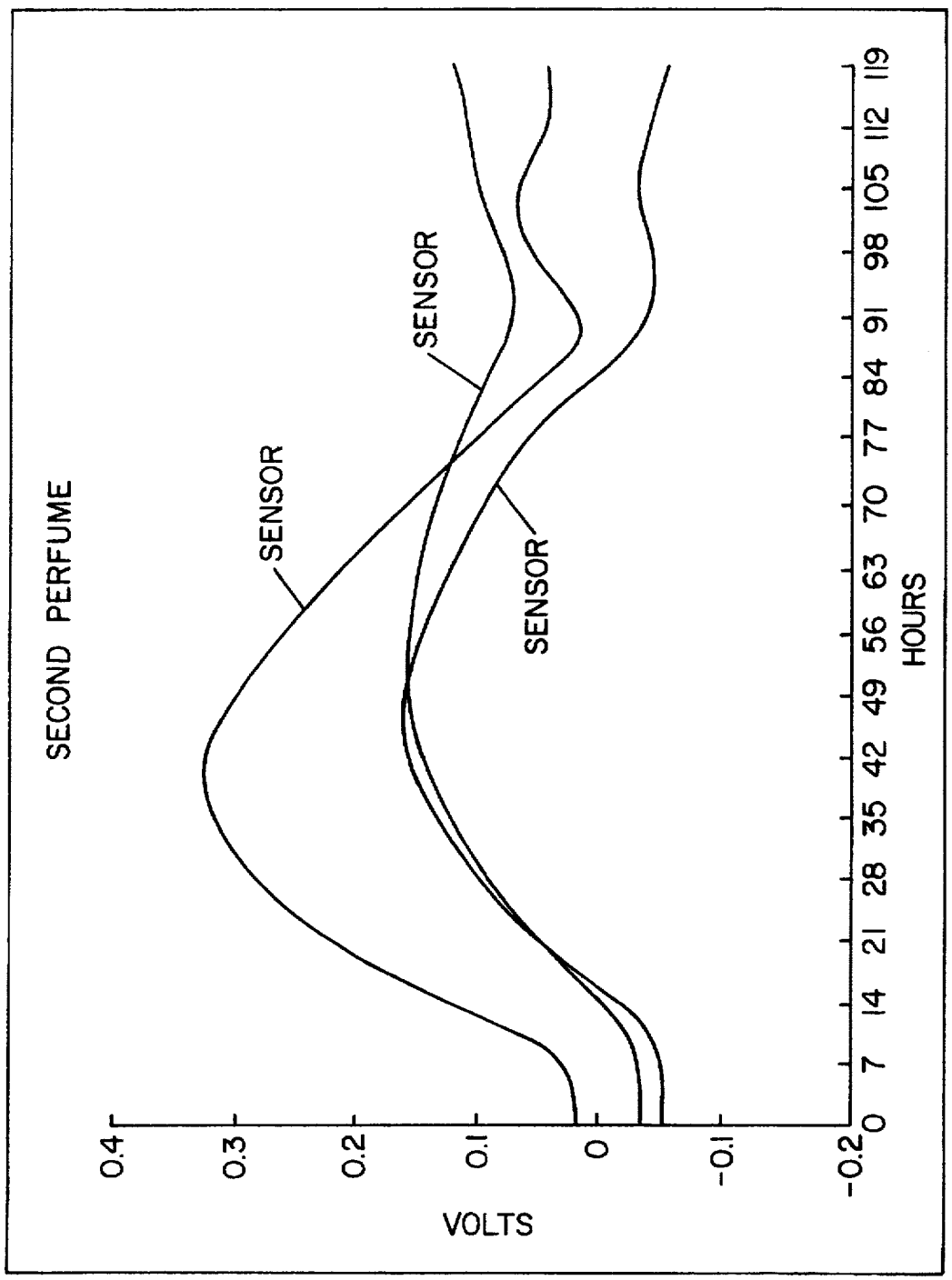
FIG. 9 shows a diagram of an olfactory characteristic of odorous substances coming from a perfume different from the one used in FIG. 8.

A third experiment was performed with a first and second type of perfume, shown in FIGS. 8 and 9.

FIG. 8 shows an olfactory characteristic as a function of time of the first perfume permeated in a napkin and placed in the sample chamber heated to 40° C. One enclosure comprising seven semiconductive sensors and one enclosure comprising seven conductive-polymer sensors, in series connection, were used for this experiment which was carried out during five days with a gas flow rate of 10 ml/mn. Beforehand, the electric properties of the sensors were tested during ten hours in the presence of the napkin alone and with a gas flow rate of 10 ml/mn, in order to obtain an initialization of the sensors. The x-axis is graduated in hours, and the y-axis is graduated in volts. Significant responses of three sensors are shown in FIG. 8.

FIG. 9 shows an olfactory characteristic, as a function of time, of the second perfume permeated in a napkin placed in a sample chamber. The conditions of the experiment are identical to those concerning the first perfume, in such a way as to be able to compare the two perfumes.

The comparison of FIGS. 8 and 9 show that the perfume used in FIG. 8 has a note which is stronger and more stable in time than the perfume used in FIG. 9, the effect of which is nearly totally depleted in three days or so.

Figure 10:
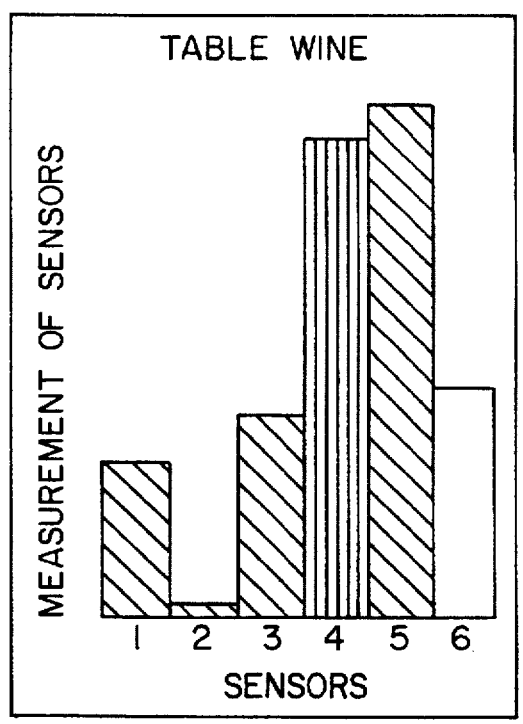
FIGS. 10, 11, and 12 show diagrams representing olfactory characteristics coming respectively from a table wine, ethanol, and the bouquet of said table wine.
Figure 11:
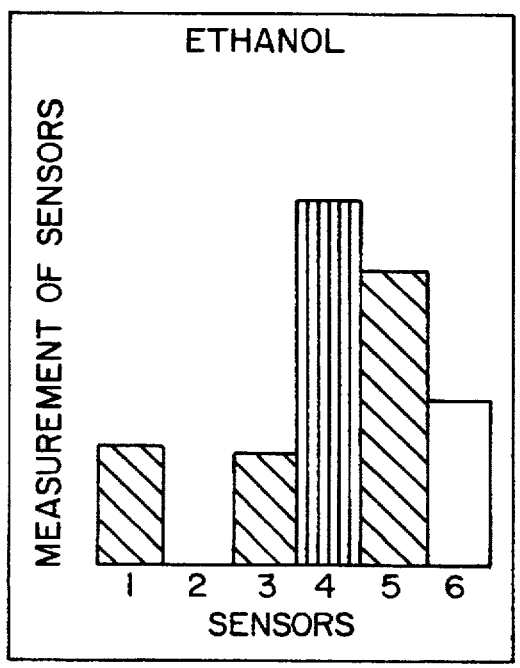
Figure 12:
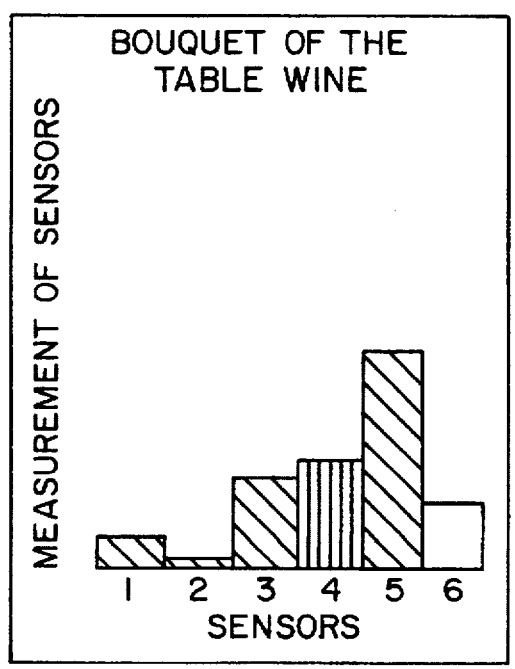

A fourth experiment was performed with a table wine and ethanol, shown in FIGS. 10, 11, 12.

The FIGS. 10, 11 and 12 show olfactory characteristic respectively, the olfactory characteristics of a table wine, of ethanol, and of the bouquet of said table wine obtained using the data processing unit from the difference of the olfactory characteristics of the wine and the ethanol. The experiment was performed using an enclosure equipped with six semiconductive sensors, a low flow rate of air, and the stabilized characteristics were obtained after around 30 seconds. Each of the six rectangles referenced from 1–6 on FIGS. 10 and 11 respectively shows the measurement of the same sensor, after about 30 seconds.

A fifth experiment was performed in order to recognize the original formulation of silicones and polymers, using two enclosures each equipped with six semiconductive sensors and four surface-acoustic-wave sensors. The residual solvents of polymer compositions such as polypropylene being the origin of certain bad odors of plastic materials, a group of sensors of different technologies detects the differences with regard to a reference odor.

A sixth experiment concerns the detection and recognition of drugs.

Drugs, such as morphine and cocaine or other illicit products, are detected using a group of sensors, including semiconductive ones, conductive-polymer ones, and surface-acoustic-wave sensors. When the surface-acoustic-wave sensors are used alone, with four sensors for example, the rate of recognition between the different drugs analyzed is 90 percent (number of drugs recognized/number of drugs analyzed). However, in the latter case, the rate of recognition diminishes to forty percent when these drugs are mixed with other products like coffee, tobacco, and other powders of current products. It is therefore necessary to use other technologies of sensors which allow one to obtain a greater selectivity in order to offer olfactory characteristics of drugs, detectable even in the presence of many different substances. The addition of six semiconductive sensors to the four surface-acoustic-wave sensors allows one to obtain a rate of recognition of 65 percent, and the supplementary addition of fourteen conductive-polymer sensors allows one to augment the rate of recognition to 85 percent.

Figure 13:
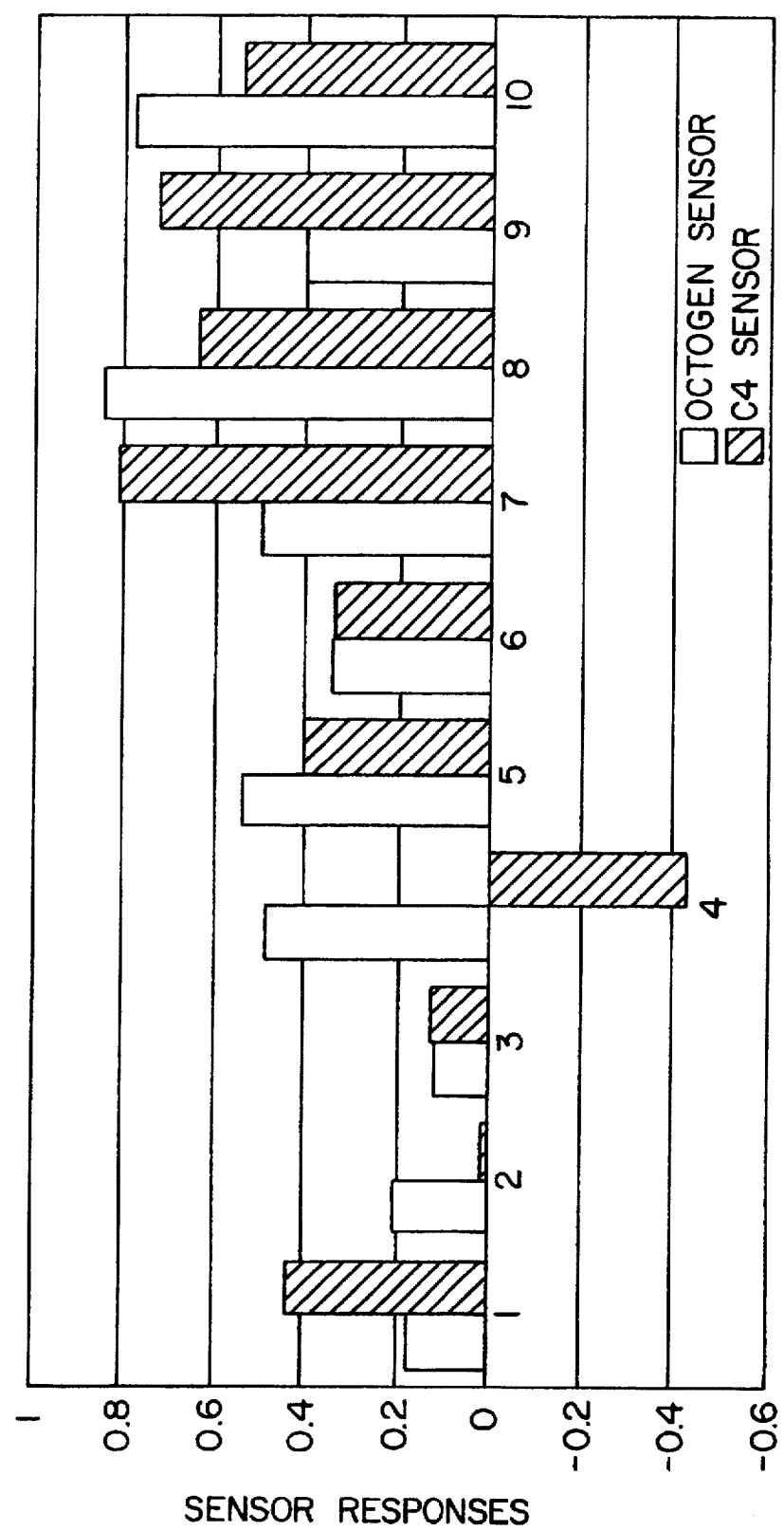
FIGS. 13, 14, and 15 show diagrams of olfactory characteristics coming from two different explosives, under different forms and different experimental conditions.
Figure 14:
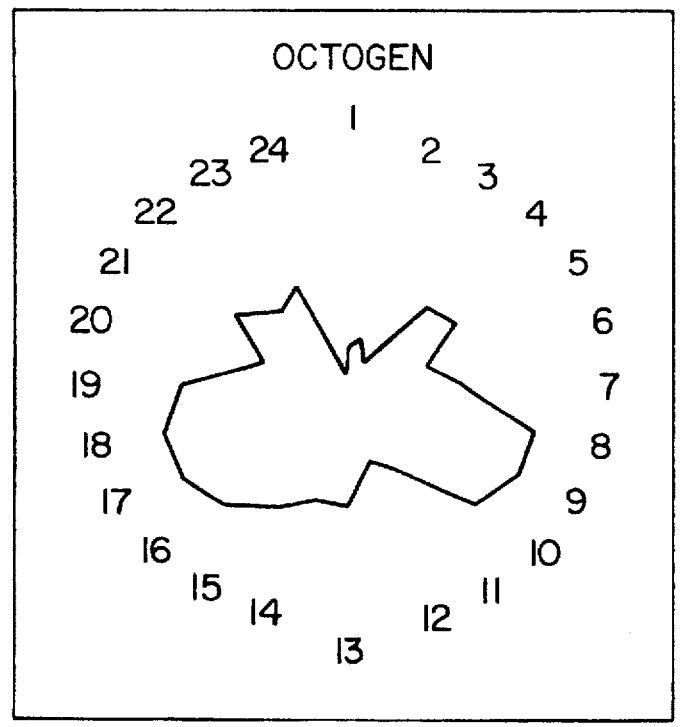
Figure 15:
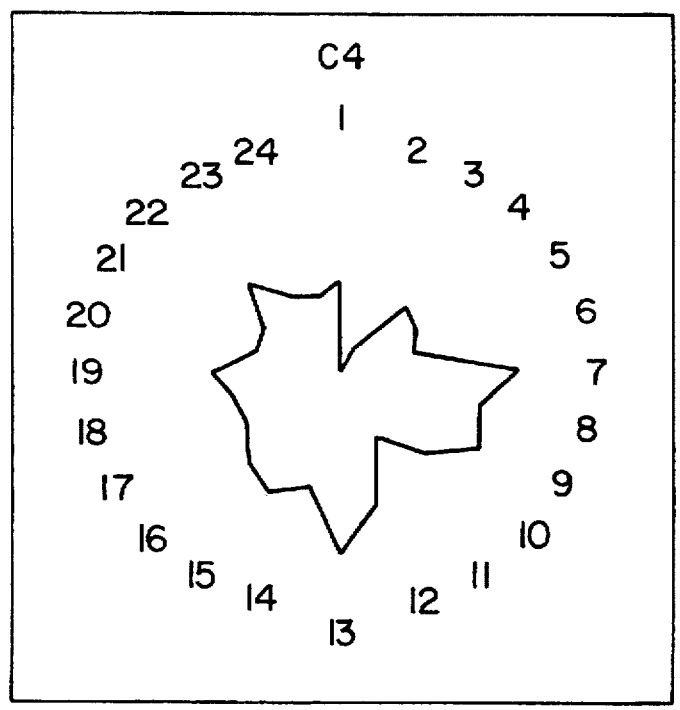

A seventh experiment concerns the detection and recognition of explosives, illustrated by FIGS. 13, 14 and 15.

FIG. 13 shows olfactory characteristics of two different explosives, in the form of a histogram. The dark rectangles represent an explosive of type C4 and the clear rectangles represent an explosive of the octogen type (HMX). The values of each sensor for each of the explosives are shown side by side to facilitate a comparison. To realize this experiment, there was used a group of four surface-acoustic-wave sensors and six semiconductive sensors. The olfactory characteristics of the explosives were previously recorded in the memory of the data processing system, which makes it possible to identify and to recognize an explosive later on from its volatile substances. On the x-axis, the references 1–4 correspond to the surface-acoustic-wave sensors, and the references 5–10 correspond to the semiconductive sensors. It is to be noted that the frequency variation of the sensor referenced 4, due to a viscoelastic effect characteristic of the coating of the sensor, makes up an important element of the characteristic serving to discriminate the explosive C4 from the octogen type explosive.

FIGS. 14 and 15 show olfactory characteristics of the same explosives, respectively octogen type and C4. These characteristics were obtained with a group of sensors similar to those used in FIG. 13, to which were added fourteen conductive-polymer sensors, that is to say a total of twenty-four sensors. On FIGS. 14 and 15, the diagrams are shown in the shape of a star, the references 1–4 corresponding to the surface-acoustic-wave sensors, the references 5–10 corresponding to the semiconductive sensors, and the references 11–24 corresponding to the conductive-polymer sensors. One notices a clear difference between the diagrams, characteristic of each explosive.

Figure 16:
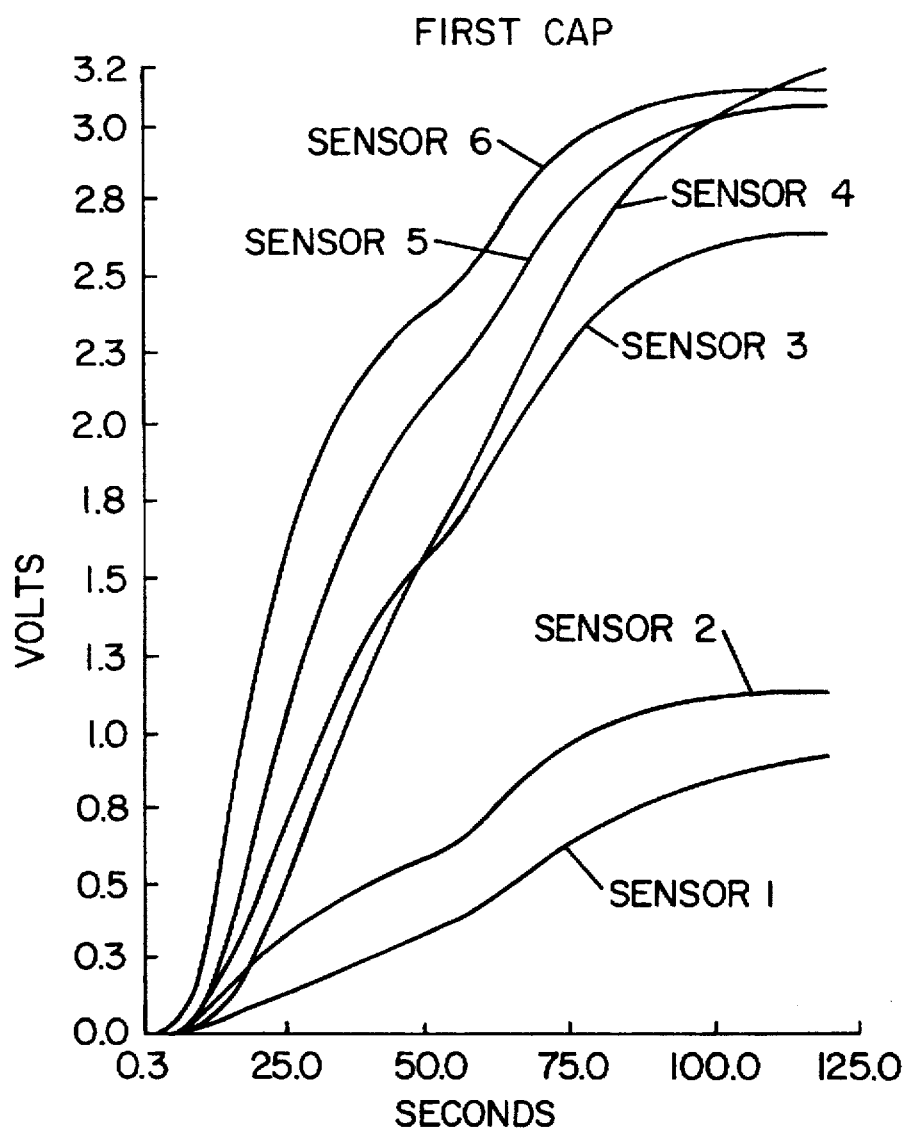
FIGS. 16 and 17 show diagrams of olfactory characteristics as a function of time coming from two cork caps.
Figure 17:
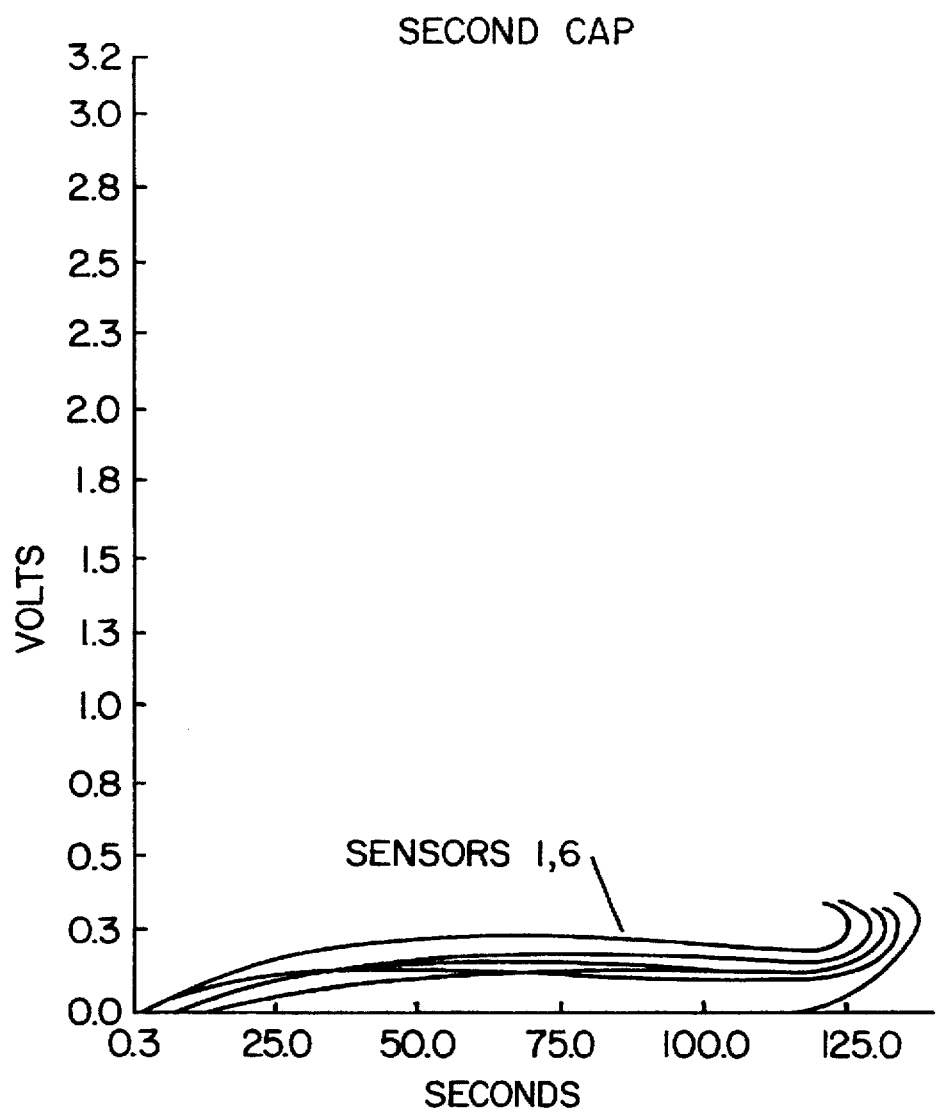

An eighth experiment involves the detection and recognition of odors of a cap made of cork, illustrated in FIGS. 16 and 17.

A first and second cap were respectively placed in a first and second sample chamber, of 60 ml each, and heated to 60 degrees C. for 5 mn. The vapors of the two caps are then transported successively into the enclosure equipped with six semiconductive sensors. FIGS. 16 and 17 respectively show the olfactory characteristics obtained for the first and second cap, during 120 seconds. One observes a clear difference of the graphical characteristics, showing that the first cap is not appropriate for use or presents a risk of contaminating the product enclosed by the cap, given the stronger intensity of odors, and shapes which characterize bad odors from caps. The second cap shows a correct standard characteristic and is good for use. It will advantageously be noted that the method according to the invention provides, in this case, the ability to make an olfactory selection of caps at the time of their production and thus avoids the loss of products capped with caps that are defective and contaminated thereby, notably for wines and spirits.

A ninth experiment involves the detection and recognition of human body odors.

Body odors are analyzed by placing a subject in a first chamber with a through flow of clean air. The air bearing the odorous substances released by the subject then flows into a second chamber which is substantially less voluminous, and which concentrates the volatile compositions. This second chamber can be made up of a trap (Tenax) or other polymer supports which can absorb. By a rapid reheating of the second chamber after the concentration of the volatile compositions, the air flow with the odorous substances from the subject is sent over the group of sensors, which can advantageously include a plurality of semiconductive sensors. The measurement data from the sensors is simultaneously compared to a file of odorous substances of criminals or individuals who have already been incriminated, with the goal of recognizing the subject.

It should be mentioned that the second chamber is dispensable to the process of detecting and recognizing body odors according to the invention. The air with the odorous substances released by the subject in the first chamber can be directly sent to the sensors, the utilization of a concentrator having as its object, notably, to improve the quality and rapidity of the production of the olfactory characteristic.

A tenth experiment involves the detection and recognition of animal odors.

A device according to the invention including a plurality of conductive-polymer sensors was placed in such a way as to detect odorous substances coming from the genital areas of a mare. One obtains an olfactory graph which is characteristic of the fertile period of the animal. Olfactory graphs characteristic of the fertile period of an animal were obtained in a similar way by following the periods of fertility in a cow and a bitch.

It is possible to proceed to a test of fertility of a cow by measuring the vapors emitted by its milk. The fertile period induces in the milk volatile compositions responsible for a series of responses which are characteristic of a fertile animal.

As one can observe, the field of the applications of the processes and the apparatus for detecting odorous substances according to the invention is very large, the experiments described above only illustrate some examples of this field of application.

One could also cite, by way of non-limiting examples, the following applications of the processes and apparatus according to the invention:

- detecting and measuring the efficacy of deodorants and bacterial odors by direct contact of a device according to the invention under the armpit of different subjects;
- evaluating the pleasant or unpleasant character of the odor;
- diagnosing illnesses from body smell;
- aromatic discrimination of the quality of beans and blends of coffee, monitoring the process of roasting;
- distinguishing different olfactive qualities of olive oils (bitter, fruity, etc.) ... resulting from particular climatic conditions or treatments;
- continuous measurement of enclosed environments; inspecting smoke-filled environments possibly with an alarm threshold (or monitoring of ventilation) based on a predetermined threshold level of pollution;
- measuring the intensity and the quality of the odor of polyethylene particles of PVC, of silicones and other plastic materials;
- monitoring odor in finished plastic materials and evaluating the individual contribution of each component to the global odor of a dwelling place (interior of cars, of shuttles, etc.);
- checking the hydrocarbons and residual odors in the inside of plastic bottles; and
- based on meat, discriminating the sex of the animal of origin.

The invention has been described in detail, with particular emphasis being placed on preferred embodiments, but variations and modifications within the spirit and scope of the invention will occur to those skilled in the art and from the appended claims.

We claim:

1. A process for analyzing odorous or volatile substances using an apparatus including:
   a first enclosure having a first detection means, said first detection means comprising a plurality of gas sensors using a same first technology selected from semiconductor gas sensors technology, or conductive polymer gas sensors technology, or acoustic surface wave gas sensors technology,
   a second enclosure having a second detection means, said second detection means comprising a plurality of gas sensors using a same second technology selected from semiconductor gas sensors technology, or conductive polymer gas sensors technology, or acoustic surface wave gas sensors technology, said second technology being different from said first technology,
   said semiconductor gas sensors, conductive polymer gas sensors and acoustic surface wave sensors having electrical or piezo-electrical properties sensitive to molecules of the odorous or volatile substances, said process comprising the steps of:
   determining electrical or piezo-electrical properties of the first and second detection means by contacting the first and second detection means with a variable gas discharge to initialize the first and second detection means;
   transporting the odorous or volatile substances of a first sample to the first and second enclosures by a variable controlled gas discharge;
   measuring electrical or piezo-electrical properties of the first and second detection means, during a determined measurement time interval, in the presence of a variable controlled gas discharge containing the odorous or volatile substances of the first sample, wherein relative to the electrical or piezo-electrical properties during initialization, to obtain qualitative data and quantitative data for the odorous or volatile substances of the first sample;
   comparing said qualitative data of the first sample with a file of odorous or volatile substances, simultaneously with the step of measuring or after the step of measuring, the comparison occurring during the measurement time interval, to identify or recognize the odorous or volatile substances detected by means of the network of neurons; and
   cleaning the first and second detection means with a gas, in order to reinitialize the first and second detection means.

2. A process according to claim 1, characterized in that said apparatus includes at least a third enclosure having a third detection means, said third detection means comprising a plurality of gas sensors using a same third technology selected among semiconductor gas sensors technology, or conductive polymer gas sensors technology, or surface acoustic wave gas sensors technology, said third technology being different from said first and second technologies.

3. A method according to claim 2, wherein said first, second, and third enclosures are arranged in series.

4. A method according to claim 2, wherein said first, second, and third enclosures are arranged in parallel.

5. A process according to claim 1, wherein said first and second enclosures are arranged in series.

6. A process according to claim 1, wherein said first and second enclosures are arranged in parallel.

7. Process according to claim 1, wherein the odorous or volatile substances are separated by means of a gas chromatography device.

8. A process according to claim 1, wherein the odorous or volatile substances are analyzed to detect or recognize drugs and/or explosives.

9. A process according to claim 1, wherein the odorous or volatile substances are from a human body and are analyzed to provide identification and/or recognition of an individual.

10. A process according to claim 1, wherein the odorous or volatile substances are human body odors and are analyzed to diagnose human illnesses.

11. A process according to claim 1, wherein the odorous or volatile substances are animal odors and are analyzed to determine the period of fertility of an animal or to diagnose an animal illness.

12. A process according to claim 1, wherein the odorous or volatile substances are from caps or seals for food, and are analyzed to differentiate and/or select the quality of the seals or caps for food.

13. A process according to claim 1, wherein the odorous or volatile substances are from food substances, and are analyzed to differentiate and/or compare the quality and/or digestibility of the food substances.

14. A process according to claim 1, wherein the odorous or volatile substances are perfumes and/or cosmetics, and are analyzed to evaluate the sensory characteristics of the perfumes and/or cosmetics.

15. A process according to claim 1, wherein the odorous or volatile substances are toxic substances, and are analyzed to determine and/or check the level of pollution provided by the toxic substances.

16. A process according to claim 1, wherein the odorous or volatile substances are plastic materials, and are analyzed in order to evaluate the individual olfactory contribution to the total odor and/or in order to inspect the total odor of the plastic materials.

17. A method according to claim 1, wherein said first technology is semiconductor gas sensors technology and said second technology is conductive polymer gas sensors technology.

18. A method according to claim 1, wherein said first technology is semiconductor gas sensors technology and said second technology is surface acoustic wave gas sensors technology.

19. A device for analyzing odorous or volatile substances, comprising:

a first enclosure including a first detection means having electrical and/or piezo-electrical properties sensitive to molecules of the odorous or volatile substances, said first detection means comprising a plurality of gas sensors using a same first technology selected from semiconductor gas sensors technology, or conductive polymer gas sensors technology, or acoustic surface wave gas sensors technology;

a second enclosure including a second detection means having electrical and/or piezo-electrical properties sensitive to molecules of the odorous or volatile substances, said second detection means comprising a plurality of gas sensors using the same second technology selected among semiconductor gas sensors technology, or conductive polymer gas sensors technology, or acoustic surface wave gas sensors technology, said second technology being different from said first technology;

pump means for variably discharging a gas;

means for testing and measuring the electrical and/or piezo-electrical properties of said first and second sensing means to obtain qualitative and quantitative data on the odorous or volatile substances; and means for comparing the qualitative data with a file of odorous or volatile substances to identify or recognize the odorous or volatile substances using a neural network.

20. An apparatus according to claim 19, further comprising at least a third enclosure, said third enclosure including a third detection means, said third detection means comprising a plurality of gas sensors using a same third technology selected from semiconductor gas sensors technology, or conductive polymer gas sensors technology, or acoustic surface wave gas sensors technology, said third technology being different from said first and second technologies.

* * * * *